(12) United States Patent
Shi et al.

(10) Patent No.: US 10,864,220 B2
(45) Date of Patent: Dec. 15, 2020

(54) APPLICATIONS OF DESOGESTREL IN THE PREPARATION OF ANTI-COLON CANCER/BREAST CANCER ER-NEGATIVE AH RECEPTOR-POSITIVE PRODUCTS

(71) Applicant: SHANGHAI JIAO TONG UNIVERSITY, Shanghai (CN)

(72) Inventors: Yongyong Shi, Shanghai (CN); Zhijian Song, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 15/740,763

(22) PCT Filed: Jun. 30, 2015

(86) PCT No.: PCT/CN2015/000473
§ 371 (c)(1),
(2) Date: Dec. 28, 2017

(87) PCT Pub. No.: WO2017/000078
PCT Pub. Date: Jan. 5, 2017

(65) Prior Publication Data
US 2018/0185387 A1    Jul. 5, 2018

(51) Int. Cl.
*A61K 31/567* (2006.01)
*A61P 35/00* (2006.01)

(52) U.S. Cl.
CPC ............ *A61K 31/567* (2013.01); *A61P 35/00* (2018.01)

(58) Field of Classification Search
CPC ............................... A61K 31/567; A61P 35/00
See application file for complete search history.

(56) References Cited

U.S. PATENT DOCUMENTS

| 2003/0050288 | A1 | 3/2003 | Grubb et al. |
| 2004/0126785 | A1* | 7/2004 | Li .................... A61K 48/0058 435/6.14 |
| 2005/0234251 | A1* | 10/2005 | Grisenti ................ C07J 1/0059 552/623 |

FOREIGN PATENT DOCUMENTS

| CN | 101181638 A | 5/2008 |
| WO | WO-03/082299 A1 | 10/2003 |

OTHER PUBLICATIONS

Schindler, "Long-term use of progestogens: Colon adenoma and colon carcinoma," Gynecological Endocrinology, Oct. 2007; 23(S1): 42-44. (Year: 2007).*
International Search Report and Written Opinion (ISA/CN) for International Application No. PCT/CN2015/000473, dated Mar. 23, 2016.

(Continued)

*Primary Examiner* — Theodore R. West
(74) *Attorney, Agent, or Firm* — Foley & Lardner LLP

(57) ABSTRACT

This invention discloses applications of desogestrel in the preparation of anti-colon cancer/breast cancer ER-negative Ah receptor-positive products. This invention provides applications for desogestrel in the preparation of products to treat colon cancer and/or breast cancer. From carrying out cancer drug repositioning for the FDA- and CFDA-approved drug desogestrel, experiments for this invention show, based on screening of non-anti-cancer drugs for various cancer cell lines (tissue types) and mutation sites, that desogestrel has a new use as an anti-colon cancer medication, thus achieving a new purpose for an old drug.

4 Claims, 2 Drawing Sheets

(56) References Cited

OTHER PUBLICATIONS

Kumar et al., Nestorone®: a progestin with a unique pharmacological profile, Steroids 65, 2000, 8 pages.
P. Raigoso et al., "Estrogen and progesterone receptors in colorectal cancer and surrounding mucosa", The International Journal of Biological Markers, vol. 16 No. 4, 2001, pp. 262-267.

* cited by examiner

|   | 1 | 2 | 3 | 4 | 5 | 6 | 7 | 8 | 9 | 10 | 11 | 12 |
|---|---|---|---|---|---|---|---|---|---|----|----|----|
| A |   | S1208(→) | | | | | | | | | | S1208 |
| B | DMSO | Cpd1(→) | | | | | | | | | | |
| C |   | | | | | | | | | | | |
| D |   | Cpd2(→) | | | | | | | | | DMSO | |
| E |   | | | | | | | | | | | |
| F | S1208 | Cpd3(→) | | | | | | | | | | DMSO |
| G |   | | | | | | | | | | | |
| H |   | S1208(→) | | | | | | | | | | |
Figure 1
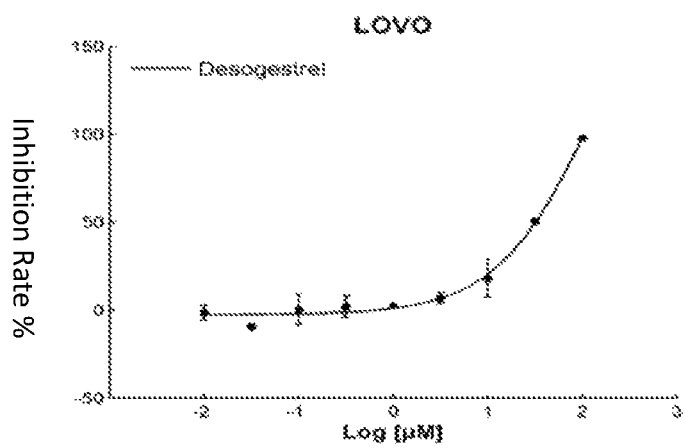
Figure 2
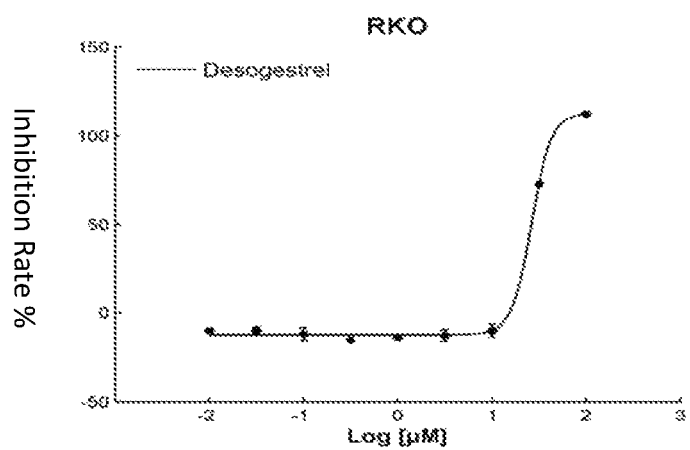
Figure 3

APPLICATIONS OF DESOGESTREL IN THE PREPARATION OF ANTI-COLON CANCER/BREAST CANCER ER-NEGATIVE AH RECEPTOR-POSITIVE PRODUCTS

CROSS-REFERENCE TO RELATED APPLICATION

This application is a national phase entry under 35 U.S.C. § 371 of International Application No. PCT/CN2015/000473, filed Jun. 30, 2015, the content of which is hereby incorporated by reference in its entirety.

TECHNICAL FIELD

The present invention relates to the technical field of biology, and it particularly relates to the application of desogestrel in the preparation of anti-colon cancer/breast cancer ER-negative Ah receptor-positive products.

BACKGROUND

Cancer is the most common as well as the most serious disease that threatens human health, and developing effective anti-cancer medications is critical to extending patients' lives. Along with the rapid development of cancer genomics and molecular pharmacology in recent years, the development of new anti-cancer medications has had relatively good outcomes. However, since the bottlenecks of large investments required in the development of new medications and the long-time periods cannot be overcome, as well as the great individual variation in tumor genetics, many traditional anti-cancer medications are not very effective, new medications are expensive, and side effects are not well understood.

In a paper published by the researchers Barabasi A L et. al. in the 2011 Nature Reviews Genetics, a molecular network analysis conducted based on GWAS findings and an interactome strategy is expected to reveal new drug targets and molecular markers for complex diseases, and ultimately to provide an entirely new understanding of disease pathogenesis and treatment approaches. Even more noteworthy is that it has been discovered in drug repositioning studies that susceptibility genes locked in by GWAS studies as well as their genes with protein-protein interaction (PPI) can more easily become indirect targets for medications. This discovery aids in explaining the mechanisms of action of currently available drugs as well as guiding new drug research. In 2014, researchers Okada Y et. al. published a paper in Nature showing that out of the 101 susceptibility genes for rheumatoid arthritis found through a meta-analysis of GWAS findings, 98 are currently being used as direct or indirect targets for rheumatoid arthritis medications. They also discovered through drug repositioning research that there are dozens of medications that have been approved for use for other indications that could be used to treat rheumatoid arthritis.

DISCLOSURE

This research was carried out through integrating cancer gene profiles of the Cancer Gene Census of the Cosmic version 72 cancer histological database as well as the protein interactions in the STRING version 10 database with Drug Bank Version 4.2, the database of FDA approved medications. This obtained candidates for drug repositioning and screening tests for tumor cell lines were carried out, revealing new anti-cancer drugs. Candidates for tumor suppressing drugs revealed from the cancer cell line screening are as follows:

nicardipine, promethazine, estrone, desogestrel, sulindac, estradiol, etonogestrel, levonorgestrel, mesalazine, indomethacin, sulfasalazide, balsalazide, irbesartan, ibuprofen, isoprenaline, and pentosan polysulfate.

The primary goal of this invention is to provide a new use for desogestrel.

This invention provides applications for desogestrel in the preparation of products to treat colon cancer and/or breast cancer.

The second goal of this invention is to provide a new use for desogestrel.

This invention provides applications for desogestrel in the preparation of products to inhibit the proliferation of colon cancer cells and/or breast cancer cells.

The second goal of this invention is to provide a new use for desogestrel.

This invention provides applications for desogestrel in the preparation of products to reduce IC50 values in colon cancer cells and/or breast cancer cells.

Use of desogestrel in treating colon cancer and/or breast cancer are also within scope of protection of this invention.

Use of desogestrel in inhibiting the proliferation of colon cancer cells and/or breast cancer cells are also within scope of protection of this invention.

Use of desogestrel as a medication for treating colon cancer and/or breast cancer are also within scope of protection of this invention.

Use of desogestrel as a medication for inhibiting the proliferation of colon cancer cells and/or breast cancer cells are also within scope of protection of this invention.

In the applications above, the colon cancer cells referred to are LoVo or RKO; the breast cancer referred to is ER-negative Ah receptor-positive breast tumors, and the breast cancer cells referred to are specifically MDA-MB-468.

In the applications above, the product is a medication or reagent kit.

The fourth goal of this invention is to provide a new use for desogestrel.

The active ingredient in the product of this invention is desogestrel, and it has at least one of the following functions:

1) Treatment of colon cancer and/or breast cancer;
2) Inhibition of the proliferation of colon cancer cells and/or breast cancer cells;
3) Reduction of IC50 values of colon cancer cells and/or breast cancer cells;

In the product above, the colon cancer cells referred to are LoVo or RKO; the breast cancer referred to is ER-negative Ah receptor-positive breast tumors, and the breast cancer cells referred to are specifically MDA-MB-468.

In the product above, the product is a medication or reagent kit.

BRIEF DESCRIPTION OF THE DRAWINGS

FIG. 1 is a distributed 96-well drug screening culture plate.

FIG. 2 is desogestrel sensitivity to colon cancer; EC50=136.2267; IC50=32.0768; $R^2$=0.9921.

FIG. 3 is desogestrel sensitivity to colon cancer; EC50=26.3045; IC50=26.2417; $R^2$=0.9988.

BEST MODE TO CARRY OUT THE INVENTION

Figure 4:
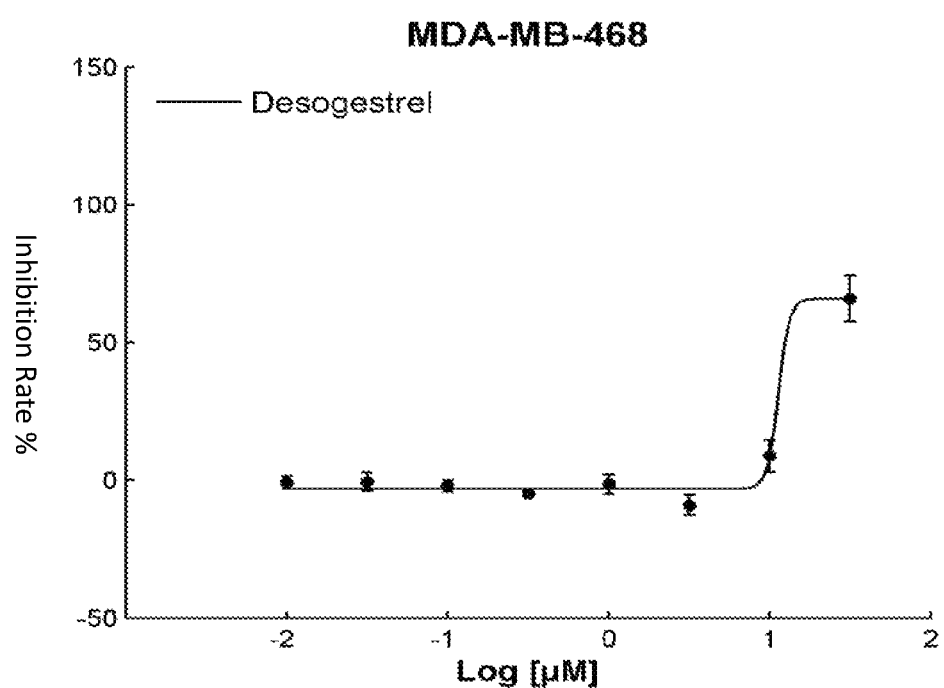
FIG. 4 is desogestrel sensitivity to ER-negative Ah receptor-positive breast cancer; EC50=11.3284; IC50=12.4694; $R^2$=0.9872.

Unless otherwise specified, the experimental methods employed in the following examples are standard methods.

Materials, reagents, etc. used in the following examples are all commercially available unless otherwise specified, and the experimental methods employed in the following examples are standard methods.

The analyte drug in the following examples is desogestrel, and its chemical composition is:

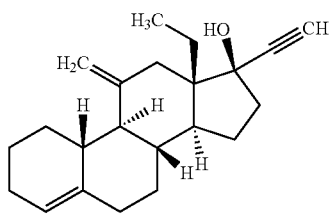

It is a drug bank product with a catalog number of DB00304.

In the examples below, the product sources for the LoVo or RKO colon cancer cells, the ER-negative Ah receptor-positive MDA-MB-468 breast cancer cells, and the BT-474 ductal breast cancer cells are:

LoVo ATCC CCL-229
RKO ATCC CRL-2577
MDA-MB-468 ATCC HTB-132
BT-474 ATCC HTB-20

The primary instruments and materials in the examples below are:

DMSO (from Sigma, Cat. No. D4540)
96-well clear bottom cell culture plates (from Corning, Cat. No. 3610)
CellTiter Glo reagent kit (from Promega, Cat. No. G7573)
Doxorubicin positive medication (from MCE, Cat. No. HY-15142)
Fetal Bovine Serum (from Gibco, Cat #10099141)
100 mm petri dish (from Corning, Cat #430167)
RPMI-1640 medium (from Gibco, Cat #A1049101)
DMEM medium (from Gibco, Cat #11995081)
DMEM/F12 medium (from Gibco, Cat #11330057)
EMEM medium (from Gibco, Cat #10370021)
Multidrop 384 cell dispensers (Thermo, Cat #5840150)
EnSpire multi-function plate reader (Perkin Elmer, Cat #2300-001M)
Ductal breast cancer cells BT-474, complete medium basis of RPMI-1640 (a live product), Cat #A1049101, with a cells/well density of 4,000.

In example 1, CELLTITER-GLO was used to test desogestrel for colon cancer

A. Test Plate Preparation
1. Cell Plating
a) The complete medium required for each cell was prepared.
b) Before beginning the experiment, the name of the drug screened for the cells marked on the 100 mm petri dish was confirmed as well as information such as the passage time and number of passages to ensure the experiment was error-free.
c) Refer to steps d) through j) for procedures for adherent cells; refer to steps j) through l) for procedures for suspension cells.
d) When using aseptic technique, a vacuum pump was used to draw the cell culture medium.
e) 2 ml of a sterile PBS solution was used to rinse the cell surface, and a vacuum pump was used to aspirate the PBS waste.
f) A 1 ml 0.25% (w/v) Trypsin-0.038% (w/v) EDTA solution was gently added to the petri dish for cell digestion, and after gently mixing several times, the solution covered the cell surfaces. The status of cell digestion was observed under an inverted microscope, and the trypsin digestion effect was terminated when cell shedding was about to occur.
g) 5 ml of pre-warmed 37° C. complete medium was added to the petri dishes, and a pipette was used to gently dissociate the cells in order for them to shed from the bottom of the petri dish.
h) The cells were suspended and transferred to a 15 ml or 50 ml sterile centrifuge tube and they were centrifuged at 1000 rpm for 5 minutes.
i) A vacuum pump was used to aspirate the medium with aseptic technique. 5 ml of pre-warmed 37° C. complete medium was used to resuspend the cell sediment, and it was gently dissociated to mix evenly.
j) A pipette was used to gently dissociate the cells so that they fully shed from the bottom of the petri dish.
k) The cells were suspended and transferred to a 15 ml or 50 ml sterile centrifuge tube and they were centrifuged at 1000 rpm for 5 minutes.
l) A vacuum pump was used to aspirate the medium with aseptic technique. 5 ml of pre-warmed 37° C. complete medium was used to resuspend the cell sediment, and it was gently dissociated to mix evenly.
m) A cell counter was used to count the number of suspended cells and adjust the cell suspension to an appropriate density in the plate to carry out cell plating experiments.

RKO cells, LoVo cells, and MDA-MB-468 ductal breast cancer cells were handled as described above, and RKO 96-well cell culture plates, 96-well LoVo cell culture plates, and 96-well MDA-MB-468 cell culture plates were obtained, respectively.

The complete medium for RKO cells was DMEM (a live product), Cat #11995081, with a cells/well density of 12000.

The complete medium for LoVo cells was MEM (a live product), Cat #10370021, with a cells/well density of 8000.

The complete medium for ER-negative Ah receptor-positive MDA-MB-468 breast cancer cells was Leibovitz's L-15 (a live product), Cat #11415064, with a cells/well density of 12000.

2. The Drug Analyte Desogestrel was Prepared and Administered (200× Final Concentration):
1) The master plate for the drug analyte desogestrel was prepared
a) DMSO was used to dilute the analyte desogestrel to 20 mM for use.
b) 79 μL of the 20 mM analyte prepared in step a) was added to the first well in the first row of the dilution plate, and then 54 μL of DMSO solution was added to the second through ninth wells of the first row. 25 μL of solution was aspirated from the first to the second well, and after mixing well 25 μL of solution was aspirated from the second to the third well, and this was repeated until the 9th well in order to ensure that 3.16 dilution of the medication would be carried out one-by-one.

2) Doxorubicin positive medication (MCE, Cat. No. HY-15142) master plate preparation a) DMSO was used to dilute Doxorubicin positive medication to 6 mM for use.

b) The 6 mM Doxorubicin positive medication solution was added to the dilution plate, and the DMSO solution was incrementally added to the analyte medication to 1:3.16.

3. Drug Working Board Preparation and Dosing a) The analyte drug and the positive drug sampling template is as shown in FIG. 1, within which S1208: Positive medication Doxorubicin; DMSO: Positive control well; Cpd 1, 2, and 3: Analyte drug, with a DMSO final concentration of 0.5% (DMSO compatibility).

b) 95 µl of cell-specific complete medium was added to the working plate, each medication to 9 wells. A multi-channel pipettor was used to transfer a series of 5 µl (9 wells) of the diluted solution of the analyte drug and positive medication Doxorubicin (10× final concentration) from the working plate, achieving cell culture media of varying concentrations.

c) The RKO 96-well cell plates, LoVo 96-well cell plates, and the MDA-MB-468 96-well cell plates prepared in step 1 were removed from the incubator, and 10 µl of the cell culture media (10× final concentration) with varying drug concentrations as described in b) above was added to the RKO 96-well cell culture, the LoVo 96-well cell culture, and the MDA-MB-468 96-well cell culture plate row-by-row as shown in FIG. 1. It was placed into a $CO_2$ incubator at 37° C. for 72 hours, obtaining the RKO 96-well drug screening plate, the LoVo 96-well drug screening plate, and the MDA-MB-468 96-well drug screening plate.

Wells with no medication added acted as controls.

The final concentrations and dosing of the analyte drug, positive medication Doxorubicin, and control in the 96-well plates were as follows:

The final concentrations (µM) of the analyte drug in wells 2-10 in FIG. 1 are, in order: 100, 31.64557, 10.01442, 3.16912, 1.002886, 0.317369, 0.100433, 0.031783, 0.010058;

The final concentrations (µM) of the positive medication Doxorubicin in wells 2-10 in FIG. 1 are, in order: 30, 9.493671, 3.004326, 0.950736, 0.300866, 0.095211, 0.03013, 0.009535, 0.003017;

In addition, the S1208 well in the 96-well plate (E1-H1 and A12-D12): 10 µl of final concentration 100 µM Doxorubicin solution (solvent containing 0.5% DMSO complete culture medium solution), DMSO wells (A1-D1, E12-H12, and A11-H11): 10 µl containing 0.5% DMSO complete culture medium solution.

B. CELLTITER-GLO Luminescent Cell Viability Assay System

1. CellTiter-Glo Reagent Preparation a) The CellTiter-Glo reagent buffer was thawed before using and stabilized to room temperature for use.

b) The CellTiter-Glo reagent frozen substrate was thawed before using and stabilized to room temperature for use.

c) 100 ml of stabilized CellTiter-Glo buffer was added to the container with CellTiter-Glo reagent frozen substrate to adequately resuspend it to form an enzyme/substrate mixture, also referred to as the CellTiter-Glo assay reagent.

d) It was gently mixed and vortexed and inverted multiple times to achieve a uniform solution. In general, the CellTiter-Glo substrate reagent will adequately dissolve within 1 minute. It is stored separately in low-light conditions at −20° C. to await use, and freezing repeatedly should be avoided.

2. Testing a) Before testing, the RKO 96-well drug screening plate and the LoVo 96-well drug screen plate described in 3 above were stabilized to room temperature for 20-30 minutes.

b) An inverted microscope was used to observe the conditions of each group of cells in the culture plate and their death patterns, and any abnormal conditions were noted and retested.

c) 100 µl of CellTiter-Glo reagent (prepared as described in 1 above) was added to all drug screening plates and mixed evenly.

d) It was thoroughly oscillated in a 96-well microplate oscillator for 2 minutes to allow the cells to undergo full lysis.

e) It was stored away from light at room temperature for 15 minutes before carrying out luminescent signal detection to ensure signal stability.

f) An EnSpire multi-function plate reader was used at 570 nm to read the luminescent signals.

g) Data was processed and analyzed.

The results of the RKO 96-well drug screening plate are shown in FIG. 2.

The results of the LoVo 96-well drug screening plate are shown in FIG. 3.

The results of the MDA-MB-468 96-well drug screening plate are shown in FIG. 4.

The IC50 value was calculated; results are shown in Table 1.

The same method was used to test desogestrel's action on the IC50 value of BT-474 ductal breast cancer cells; results are shown in Table 1.

It is evident that desogestrel has a specific inhibitory effect on the proliferation of colon cancer cells and it can be used as a medication for colon cancer treatment.

TABLE 1

| IC50 values of various cells under the effect of desogestrel ||
| Cells | IC50 value |
| --- | --- |
| LoVo | 32.0768 |
| MDA-MB-468 | 12.4694 |
| RKO | 26.2417 |
| BT-474 | 100 |

INDUSTRIAL APPLICATIONS

From carrying out cancer drug repositioning for the FDA- and CFDA-approved drug desogestrel, experiments for this invention show, based on screening of non-anti-cancer drugs for various cancer cell lines (tissue types) and mutation sites, that desogestrel has a new use as an anti-colon cancer medication, thus achieving a new purpose for an old drug.

What is claimed is:

1. A method for treating Dukes type C colorectal adenocarcinoma in a subject comprising administering an effective amount of desogestrel to the subject.

2. The method of claim 1, wherein the subject's colon cancer has spread to the lymph nodes.

3. A method of inhibiting the proliferation of Dukes type C colorectal adenocarcinoma cells comprising contacting the cells with an effective amount of desogestrel.

4. A method for treating a colon cancer patient with Dukes type C colorectal adenocarcinoma, the method comprising:
   (a) screening the patient having colon cancer for involvement of lymph nodes; and (b) treating the patient screened in step (a) having lymph node involvement by administering an effective amount of desogestrel to the patient.

* * * * *